United States Patent [19]
Hsia et al.

[11] Patent Number: 5,371,600
[45] Date of Patent: Dec. 6, 1994

[54] FIBER OPTIC PROBE APPARATUS AND METHOD

[75] Inventors: James C. Hsia, Andover; Rafael A. Sierra, Palmer; Michael G. Clancy, Westford, all of Mass.

[73] Assignee: Candela Laser Corporation, Wayland, Mass.

[21] Appl. No.: 928,793

[22] Filed: Aug. 12, 1992

[51] Int. Cl.⁵ .............................................. G01N 21/59
[52] U.S. Cl. ................................. 356/436; 356/440
[58] Field of Search ............... 356/432, 436, 441, 442, 356/444, 409, 414; 250/573

[56] References Cited

U.S. PATENT DOCUMENTS

| | | | |
|---|---|---|---|
| 2,324,304 | 7/1943 | Katzman | 356/442 |
| 2,580,500 | 1/1952 | Albert | 356/442 |
| 3,727,066 | 4/1973 | Louderback et al. | |
| 3,807,874 | 4/1974 | Gropper | |
| 4,188,126 | 2/1980 | Boisde et al. | |
| 4,320,977 | 3/1982 | Matsumoto | |
| 4,534,651 | 8/1985 | Minikane | |
| 4,666,672 | 5/1987 | Miller et al. | |
| 4,697,925 | 10/1987 | Hyodo et al. | 356/442 |
| 4,725,148 | 2/1988 | Endo et al. | 356/442 |
| 4,989,942 | 2/1991 | Koenigsberg et al. | |

FOREIGN PATENT DOCUMENTS

| | | | |
|---|---|---|---|
| 186158 | 11/1982 | Japan | 356/432 |
| 856617 | 12/1960 | United Kingdom | 356/442 |
| 2141537 | 12/1984 | United Kingdom | 356/409 |

*Primary Examiner*—Richard A. Rosenberger
*Attorney, Agent, or Firm*—Testa, Hurwitz & Thibeault

[57] ABSTRACT

A fiber optic probe comprises a pair of substantially parallel optical fibers separated by a gap and positioned in a centrifuge tube which contains a stratified medium. The pair of fibers includes a transmit fiber for directing light from a light source into a substantially undisturbed portion of the stratified medium disposed in the gap. Light traversing the portion of the stratified medium in the gap is collected by a receive fiber and provides an indication of a light property of the portion of the stratified medium disposed in the gap. The pair of fibers are adapted to be moved in the stratified medium without significantly disturbing the stratification of the medium. As the fibers are moved, light property measurements can be obtained in other substantially undisturbed portions of the stratified medium.

6 Claims, 4 Drawing Sheets

FIBER OPTIC PROBE APPARATUS AND METHOD

BACKGROUND

Ultracentrifugation is routinely used to separate complex biological samples into their various fractions by taking advantage of small differences in density. The fractions or gradients of the stratified sample produced by ultracentrifugation are then analyzed by many known techniques such as the use of a fractionator. To analyze a stratified sample disposed in a centrifuge tube, the fractionator first uses a mechanism to puncture the bottom of the tube. Very dense fluid is introduced through the puncture which displaces the stratified sample upwards. The displaced fluid fractions of the sample are routed through an analysis module, such as a spectrophotometer, and collected as separate samples in test tubes held in a carousel.

There are two major weaknesses of the fractionator. First, it cannot be used with all centrifuge tubes, only those soft enough to be punctured. This limitation precludes the use of glass or polycarbonate tubes. Polycarbonate tubes are particularly important since they are used in very high speed centrifuges (i.e., about 100,000 rpm or more). Also, the fractionator destroys the stratified sample during analysis, thus precluding the possibility of repeated measurements on a single sample.

SUMMARY OF THE INVENTION

In accordance with the present invention, a fiber optic probe is adapted to be moved in a sample medium for measuring a light property in substantially undisturbed portions of the medium. The probe comprises a pair of substantially parallel optical fibers rigidly separated by a gap and adapted to be positioned in the sample medium. preferably, each optical fiber has a beveled tip at its distal end which is coated with a light reflecting material. The pair of fibers includes a transmit fiber for directing light from a light source into a substantially undisturbed portion of the medium disposed in the gap. More specifically, the light is guided to the distal end of the transmit fiber and directed by the reflective tip into the gap. The light traverses the portion of the medium within the gap and is directed by the reflective tip of a receive fiber into that fiber. The light is then guided along the receive fiber to a detector for obtaining a light property measurement associated with the portion of the medium within the gap. In accordance with the present invention, the fibers are adapted to be moved in the medium without significantly disturbing the medium. As the fibers are moved relative to the medium, a spatially resolved light property measurement can be obtained for a plurality of substantially undisturbed portions of the medium.

The fiber optic probe may be positioned in a stratified medium and may measure light properties such as absorbance, fluorescence, or scattering. A particular application is that of in-situ ultraviolet absorption measurements of a lipoprotein gradient separated by ultracentrifugation.

A fiber optic probe of the present invention solves the aforementioned problems associated with analysis of a stratified media using fractionators. First, the probe is usable with any centrifuge tube including glass and polycarbonate tubes since it does not require puncturing the tube walls. The probe of the present invention enters from the open end of the centrifuge tube, so it need only be small enough to clear the walls. Secondly, the probe's fibers are not encased in a probe housing and can be quite small (i.e., less than about 1 mm in diameter), so there is essentially no disturbance of the layers of the stratified medium during the light property measurement. Any small disturbance caused by movement of the probe relative to the medium lies behind the fiber tips outside of the gap region between the fibers and does not result in measurement error. Furthermore, such disturbances are localized to a region near the fibers. By rotating the sample, a fresh portion of the stratified sample may be measured. As such, repeated property measurements can be performed with a single stratified sample since the stratification of the sample is not destroyed during measurement.

A centrifuge tube carrying stratified liquid may be mounted onto a movable stage. Accordingly, the movable stage moves the centrifuge tube along a longitudinal axis of the tube for changing the relative position of the fiber pair within the stratified liquid. As the position of the fiber pair changes relative to the stratified liquid, absorbance measurements are obtained as a function of the position of the fibers in the stratified liquid.

BRIEF DESCRIPTION OF THE DRAWINGS

The foregoing and other objects, features, and advantages of the invention will be apparent from the following more particular description of preferred embodiments of the invention, as illustrated in the accompanying drawings in which the like reference characters refer to the same parts throughout the different views. The drawings are not necessarily to scale, emphasis instead being placed upon illustrating the principles of the invention.

DETAILED DESCRIPTION OF PREFERRED EMBODIMENTS

Figure 1:
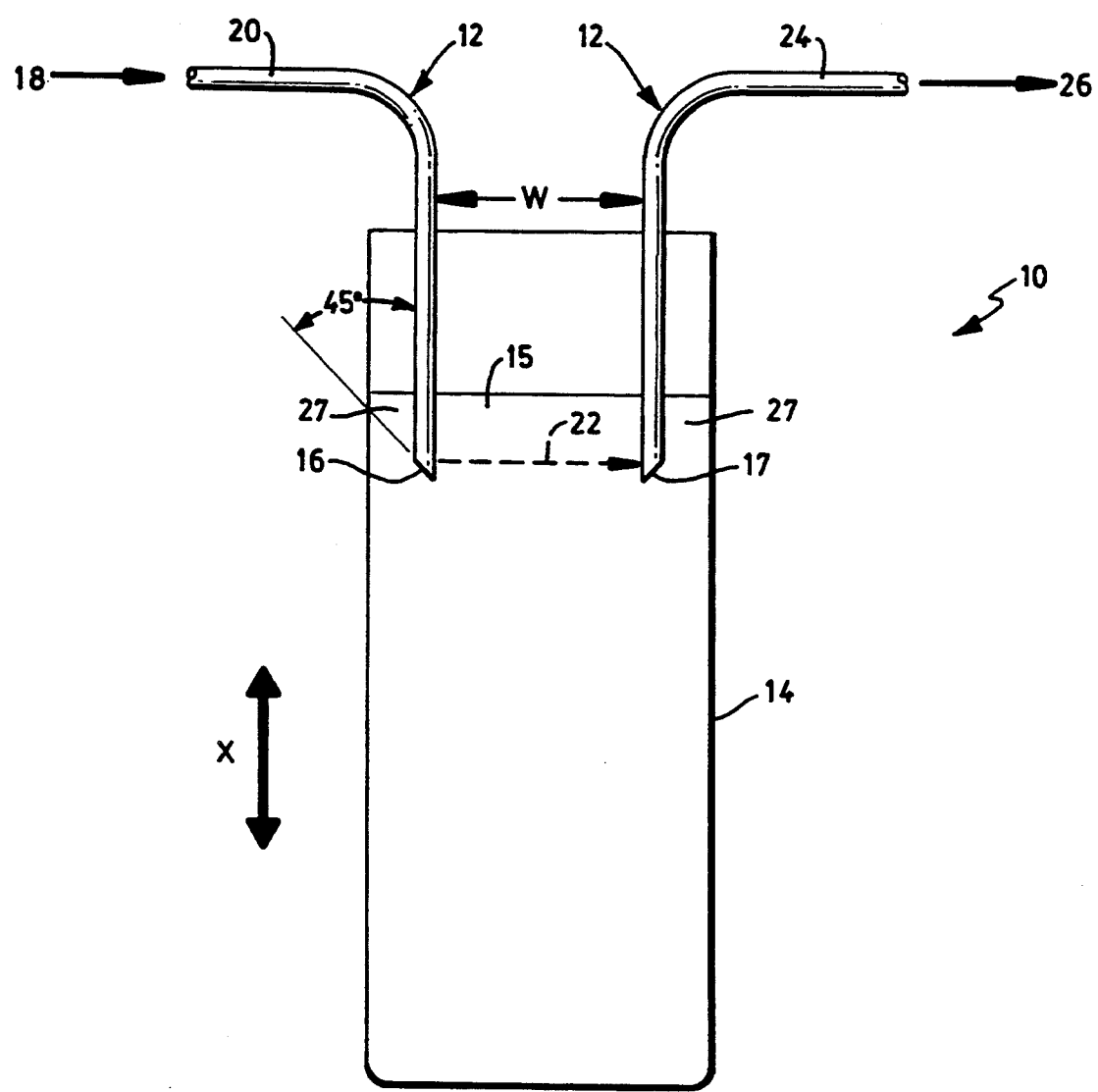
FIG. 1 is a side view illustration of an embodiment of a fiber optic probe according to tile invention.

A fiber optic probe 10 for measuring a light property, such as absorbance, of a stratified liquid sample 15 is shown in FIG. 1. The probe 10 comprises a pair 12 of small diameter optical fibers adapted to be moved in the stratified liquid 15 for obtaining a spatially resolved absorbance measurement in the x-direction without significantly disturbing the stratification of the liquid. It is noted that other light properties, such as fluorescence and scattering, can be measured without departing from the scope of the present invention. Several types of small diameter solid fibers which may be used in the present invention include 1 mm diameter HCS fibers manufactured by Ensign Bickford, 600 $\mu$m diameter ultraviolet grade PCS fibers manufactured by Ceram Optec, or 600 $\mu$m diameter all fused silica high OH fibers made by Fiberguide Industries. The preferred diameter is a function of the property measurement being made and the medium being measured. Less viscous media require smaller diameters, but smaller diameters reduce the signal to noise ratio. In general, diameters within the range of 100 to 1000 microns are preferred. Potential fiber materials can include sapphire, quartz, fluoride glass, and zinc selenide. It is noted that the present invention may also employ a pair of light guides including hollow, liquid-filled and solid light guides capable of transmitting light in the ultraviolet range to the far infrared range. Potential fiber materials include sapphire, quartz, fluoride glass, and zinc selenide.

The pair 12 of optical fibers (20 and 24) are separated by a distance (W) that is large enough for proper absorbance resolution and small enough for access into a centrifuge tube 14. In one preferred embodiment, the fibers 20 and 24 are spaced 5 mm apart and a 13.2 ml or a 1 ml glass or polycarbonate centrifuge tube is employed for housing the stratified liquid 15. The fibers 20 and 24 are cut at a preferred angle of about 45°, as shown, and the beveled distal tips 16 and 17 respectively are covered with a highly reflective coating material.

Once the fiber pair 12 is positioned in a portion 22 of the stratified liquid located in the tube 14, light 18 from an appropriate source (not shown) is focused onto the transmit fiber 20 and carried along the fiber into the centrifuge tube 14. The light reflects off of the reflective distal tip 16 of the transmit fiber 20 and exits the fiber at an angle of about 90° relative to the longitudinal axis of the fiber. The light then traverses a portion 22 of the stratified liquid 15 such that it is partially absorbed. The non-absorbed light reflects off the reflective distal tip 17 of the receive fiber 24 and is directed along the fiber to a detector (not shown). The detector converts the non-absorbed light 26 into an absorbance measurement associated with the portion 22 of the stratified liquid 15. The centrifuge tube 14 can be moved up and down in the x-direction, as indicated in FIG. 1, such that absorbance measurements can be obtained as a function of the position of the fiber pair 12 in the stratified liquid 15. Alternatively, the fiber pair 12 can be moved up and down in the x-direction.

Figure 2:
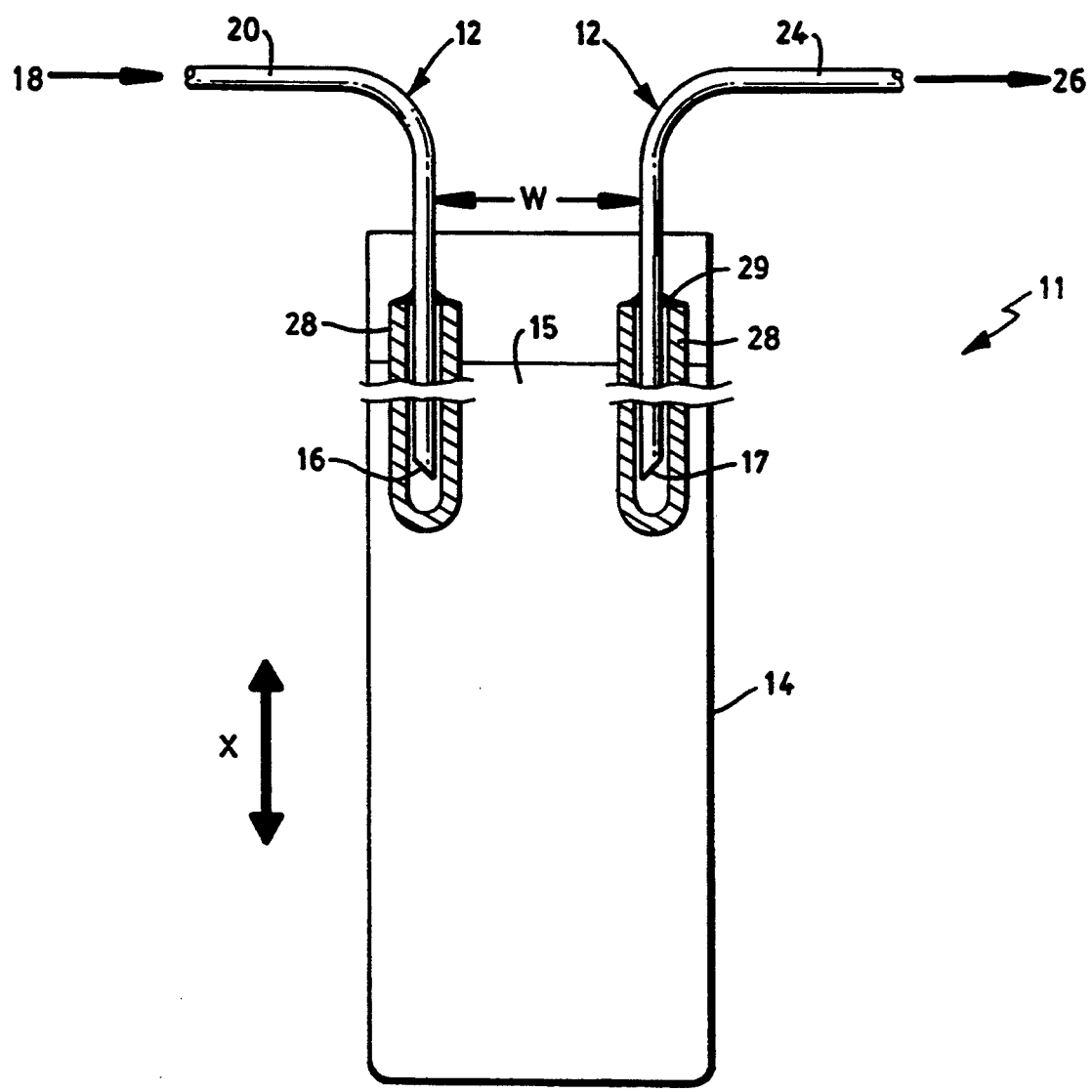
FIG. 2 is a side view illustration of an alternative embodiment of a fiber optic probe according to the invention.

It has been observed that the reflectivity of the coating materials used on the fiber pair distal tips 16 and 17 degrades when the fibers are immersed in water. The degradation appears to be accelerated by the presence of the ultraviolet radiation. Drying of the surfaces recovers some of the reflectivity, but some permanent damage does occur. Referring to FIG. 2, this problem is solved by enclosing each of the pair of fibers 12 in fused silica capillary tubes 28. Epoxy 29 is used to seal the capillary tube 28 to the fibers. These tubes 28, however, add to the dimensions of the probe 11, and may result in some increased disturbance to the stratified liquid 15. Also, since two additional surfaces are involved, this means that more than 60% of the light radiation can be lost.

To address this problem, the distal tips 16 and 17 of fibers in FIG. 1 are coated with a dielectric coating providing high reflectivity (>99%) at 45° incidence and at a wave length of 280 nm. This results in an improvement of more than a factor of two in light signal intensity. The coating is insensitive to water, thus permitting the fibers 12 to be used without protective capillary tubes. As a result, the probe 10 (FIG. 1) is at least 20% smaller in diameter for the same fiber size as the probe 11 of FIG. 2.

Referring to FIG. 1, an aspect of the present invention is that the fiber optic probe provides a spatially resolved absorbance measurement in the x-direction for the stratified liquid 15 without significantly disturbing the stratification of the liquid. Since the fibers 12 are not encased in a probe housing, the fibers alone are moved (i.e. inserted or removed) in the x-direction through the stratified medium with minimal disturbance thereto. More specifically, the fibers 12 have beveled distal tips 16 and 17 and the transmitting and receiving apertures of the fibers are at the tips, so moving the fibers in the stratified liquid 15 only disturbs an annular region 27 of the liquid behind the distal tips while the region 22 between the fibers remains undisturbed. As such, absorbance measurements can be obtained on substantially undisturbed portions of the stratified liquid.

Another aspect of the present invention is that if the diameter of the fiber pair 12 is small, the disturbance of the stratification produced by probe insertion (or removal) is small and localized around the fibers. As such, repeated insertions can be made without substantially disturbing the stratification in the bulk of the liquid. Further, if measurement of the distribution of the various layers of the stratified liquid 15 is desired, the fiber pair 12 can be rotated prior to each insertion for obtaining spatially resolved absorbance measurements along different segments of the liquid. Thus, absorbance measurements can be obtained for a plurality of essentially undisturbed portions of the stratified liquid.

Figure 3:
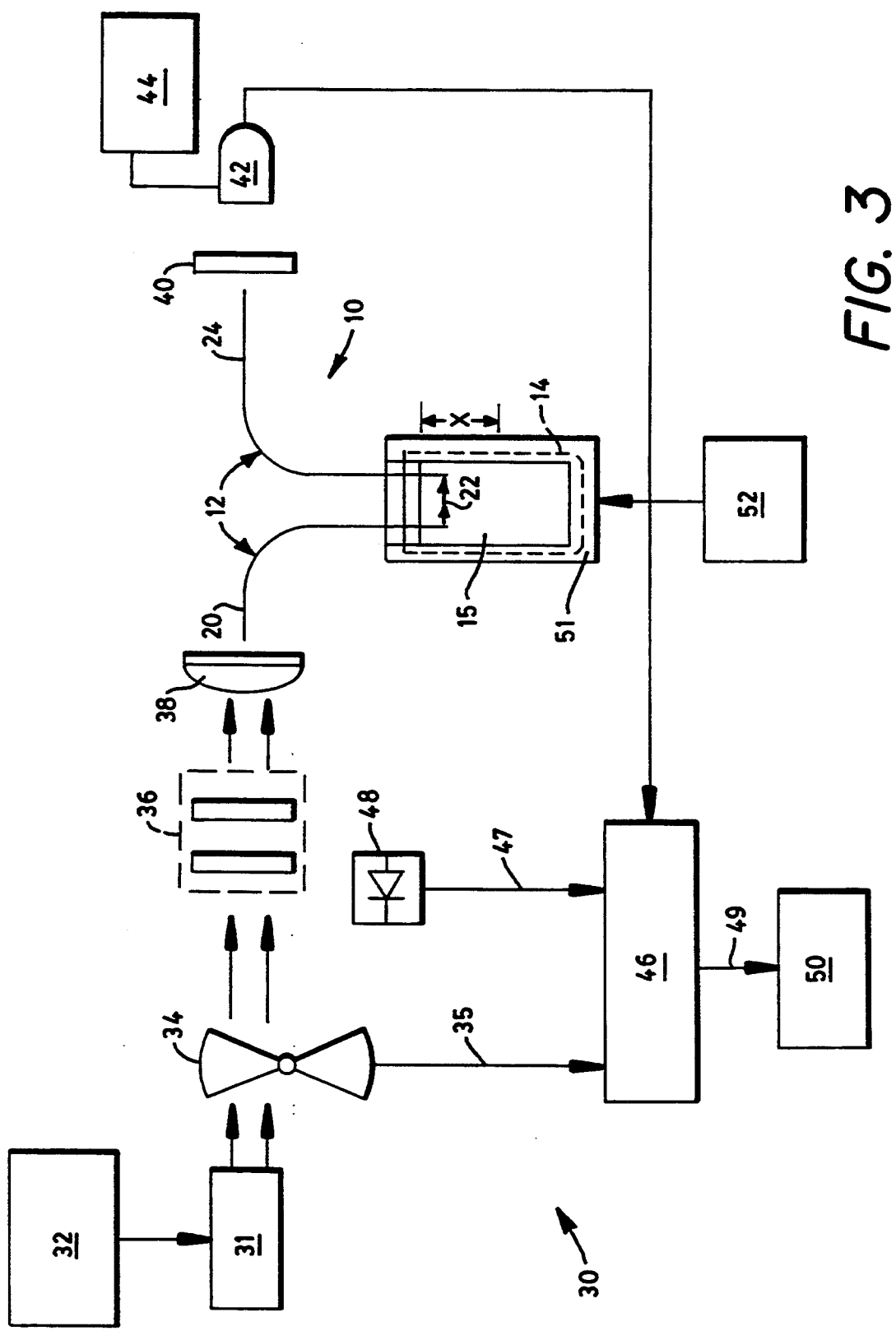
FIG. 3 is a schematic diagram of an embodiment of a fiber optic probe instrument according to the invention.

A block diagram of a lipoprotein monitoring instrument 30 employing the fiber optic probe 10 is shown in FIG. 3. A high pressure, 100 watt mercury arc lamp 31 is used as the light source. The lamp 31 is powered by a large power supply 32. Light from the lamp 32 is chopped by a mechanical chopper 34, filtered by a filter pair 36, and collimated by condensing lenses 38. The chopper 34 chops the dc lamp output at 200 Hz for use with phase sensitive detection. An ac reference signal 35 for use with phase sensitive detection is generated at the chopper 34. A dc reference signal 47 is generated by a reference detector 48 and used to normalize the output signal as described below. The filter pair 36 includes a color filter that transmits the ultraviolet and blue regions of the spectrum, and a narrow line (12 nm) interference filter centered at 280 nm.

The chopped and filtered light is focused by an 18 mm focal length lens 38 onto the proximal end of the transmit fiber 20. The light is guided by the fiber 20 to the sample region 22. The light then traverses the sample region 22 and is collected by the receive fiber 24, as described previously. The light is then guided to the detector 42. The detector 42 is a Hamamatsu 1P28 photomultiplier tube (PMT) powered by a power source 44. Directly in front of the detector 42 is another narrow band (12 nm) 280 nm filter 40. The filter 40 greatly reduces the sensitivity of the instrument 30 to stray room light, and in conjunction with the filter pair 36 adjacent to the light source 31, results in good rejection of out-of-band radiation. The output of the PMT 42 is fed into a phase sensitive lock-in amplifier 46 whose reference input has been derived from the chopper signal 35. The output 49 from the lock-in amplifier 46 is normalized using the dc reference signal 47 and then recorded as a light transmission measurement as a function of time by an IBM compatible personal computer 50.

The centrifuge tube 14 which houses the stratified sample 15 is positioned in a 10 cm travel translation stage 51. Movement of the tube 14 is controlled by the movable stage 51 which is driven by a 100 step/revolution stepper motor 52. The motor 52 is driven by a Slo-Syn stepper motor driver (not shown) whose clock is set to yield a convenient scan rate. Typically, this rate is approximately 2.5 cm/minute. Synchronization of the motor sweep with the data acquisition is effected manually by an operator.

Analysis of the data comprises converting the recorded light transmission measurements versus time into absorbance measurements versus distance in the x-direction. The distance is calculated using the known rate of travel of the sample stage 51. Absorbance measurements at a distance (d) from the top of the tube are obtained from $$A(d) = -ln(I(d)/I_o)$$

where I(d) is the transmission recorded at distance (d) in the sample and $I_o$ is the transmission in clear saline solution. The absorbance measurements are then used to derive a lipoprotein profile for the stratified liquid.

Figure 4:
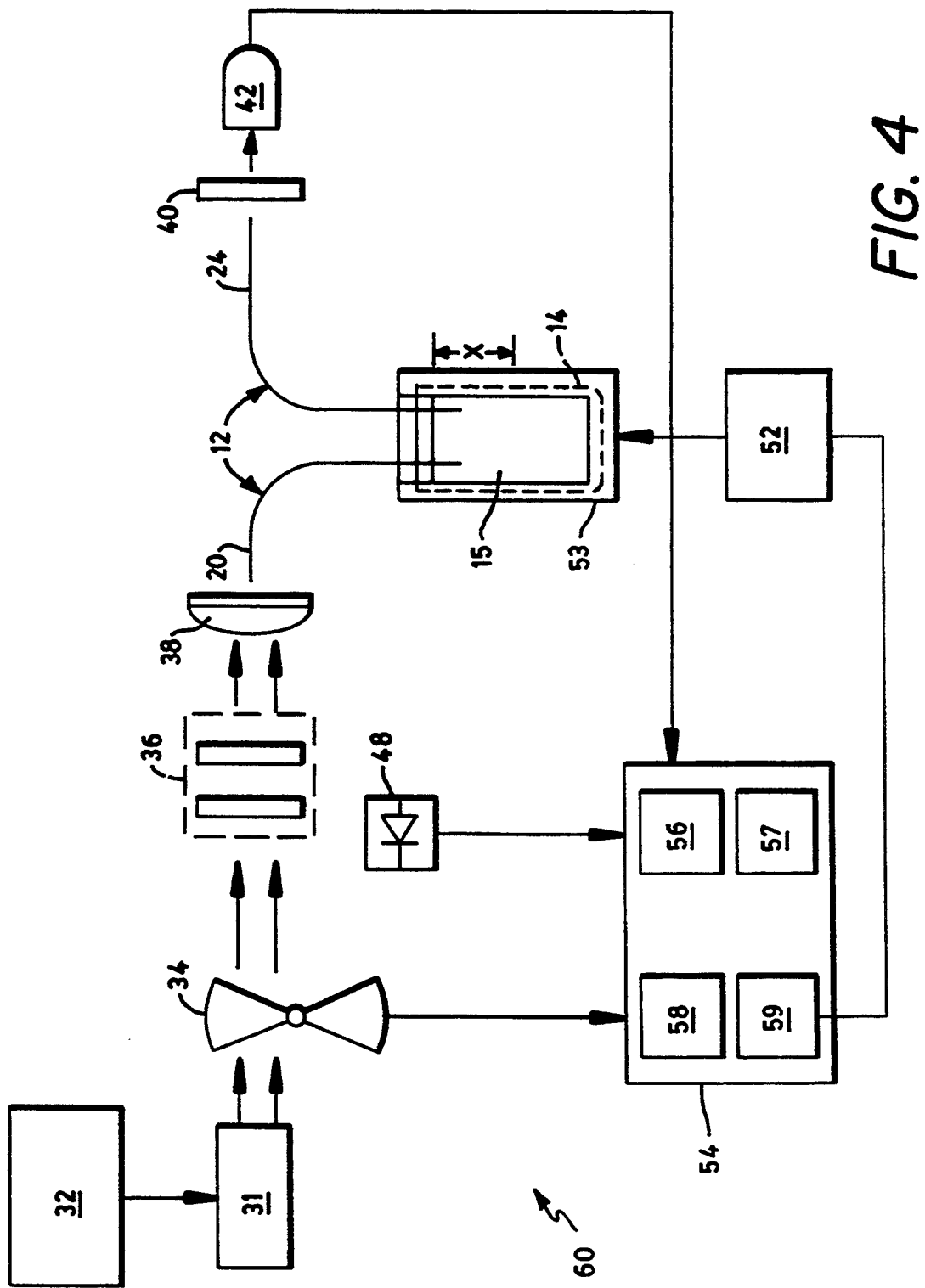
FIG. 4 is a schematic diagram of an alternative embodiment of a fiber optic probe instrument according to the invention.

A block diagram of another lipoprotein monitoring instrument 60 is shown in FIG. 4. The instrument 60 is desk-top size and most of the electronics are housed within an updated PC system 54. A comparison with FIG. 3 shows the lock-in amplifier, the motor driver, and the PMT power supply of the previously described instrument integrated into the computer system 54 for the instrument 60 of FIG. 4. Note that only the mercury arc lamp power supply 32 remains as a separate component.

An IBM compatible personal computer 56 provides processing power for the instrument 60. While the computer in the previously-described instrument 30 is used only to record the data, the computer 56 also performs the control functions. With respect to the internal modules of the computer 56, the output module is a Metrabyte μCDDA 4-channel digital and analog output module. This module interfaces directly to an IBM microchannel base and will be used to generate the analog and digital signals required to control the other modules.

The photomultiplier tube 42 gain is adjusted by varying the tube's dynode potential. The PMT supply module 57, which is integrated into the computer system 54, is a Bertram model PMT-10 programmable power supply module. This supply 57 is adjustable from 0–1 kV by means of an analog input voltage which can be provided by the computer's μCDDA board. The output from the PMT 42 is detected by the lock-in amplifier module 58. This is an Evans Electronics PSD/PCB programmable phase sensitive detector module. Programming signals for the phase sensitive detector module are also provided by the computer's μCDDA board.

The sample tube 14 is positioned in a 3 cm travel translation stage 53, and movement of the tube is effected by movement of the stage. It is expected that the instrument 60 will be particularly useful with small polycarbonate ultracentrifuge tubes that can be spun at very high speeds (e.g., 100,000 rpm) to reduce centrifuge time. The stage 53 is driven by a stepper motor 52. The motor is driven by an integrated Metrabyte MSTEP stepper motor controller 59. This module directly interfaces with the IBM computer.

EXPERIMENTAL SUMMARY

The fiber optic probe system of the present invention permits the analysis of gradients (stratified media) in ultracentrifuge tubes. The probe has been experimentally employed on a variety of centrifuge gradients and spatially resolved absorbance have been recorded. Using 13.2 ml sample tubes that had been spun for more than 48 hours at 30,000 rpm, a direct comparison has been made with spatially resolved data measured using a commercial fractionator. Excellent agreement has been observed between the features recorded using the probe system and the fractionator. The absolute absorbance, however, was higher as recorded using the probe system. The probe system has also been used to analyze gradient in small (e.g., 1 ml) tubes that had been spun for periods of the order of 1 hour at 100,000 rpm. These tubes could not be analyzed with the commercial fractionator. Several different gradients were evaluated. The probe system demonstrated that good separation of the VLD and LDL components could be achieved, although HDL remained unseparated from the bottom (d>1.2) fraction.

While the invention has been particularly shown and described with reference to preferred embodiments thereof, it will be understood by those skilled in the art that various changes in form and details may be made therein without departing from the spirit and scope of the invention as defined by the appended claims. For example, while the present invention is described as being capable of providing spatially resolved light property measurements in ultracentrifugation gradients to determine a lipoprotein profile, it can be employed for DNA and RNA analysis as well as cell sorting and other procedures, both biological and non-biological, that utilize ultracentrifugation and other stratification techniques.

What is claimed is:

1. A method of measuring an optical property of a lipoprotein gradient comprising the steps of:
    providing a pair of substantially parallel optical fibers separated by a gap;
    positioning the pair of fibers in a lipoprotein gradient such that the gradient is substantially undisturbed, the pair of fibers including a transmit fiber and a receive fiber;
    providing light to the transmit fiber which has a distal end for directing the light into a substantially undisturbed portion of the lipoprotein gradient disposed in the gap, the receive fiber having a distal end for receiving light passing through said portion of the lipoprotein gradient and directing the light into the receive fiber, the light directed into said receive fiber being indicative of an optical property of said portion of the lipoprotein gradient; and
    changing the position of the pair of fibers within the lipoprotein gradient for measuring the optical property in other substantially undisturbed portions of the lipoprotein gradient.

2. The method of claim 1 wherein the changing step comprises moving the lipoprotein gradient along a longitudinal axis parallel to the pair of fibers to change the relative position of the fibers within the lipoprotein gradient, the pair of fibers measuring the optical property in a plurality of substantially undisturbed portions of the lipoprotein gradient as the lipoprotein gradient is moved.

3. The method of claim 2 wherein the lipoprotein gradient is produced by ultracentrifugation.

4. The method of claim 1 wherein the optical property is absorbance.

5. A method of measuring absorbance of a lipoprotein gradient comprising the steps of:

providing a pair of substantially parallel optical fibers separated by a gap;

inserting the pair of fibers into a lipoprotein gradient disposed in a centrifuge tube such that the gradient is substantially undisturbed;

providing light to a first fiber of the fiber pair, the first fiber carrying light to an angular reflective surface at a distal end of the first fiber for directing the light into a substantially undisturbed portion of the lipoprotein gradient disposed in the gap, a second fiber of the fiber pair having a reflective surface at a distal end of the second fiber for receiving light and directing the light into the second fiber, the light directed into the second fiber being indicative of the absorbance of said portion of the lipoprotein gradient; and moving the pair of fibers through layers of the lipoprotein gradient for measuring the absorbance in other substantially undisturbed portions of the lipoprotein gradient.

6. The method of claim 5 further comprising removing the pair of fibers from the lipoprotein gradient, rotating the pair of fibers relative to the centrifuge tube, and repeating the inserting, providing, and moving steps to measure the absorbance in other substantially undisturbed portions of the lipoprotein gradient.

* * * * *